(12) United States Patent
Harder et al.

(10) Patent No.: US 8,840,736 B2
(45) Date of Patent: *Sep. 23, 2014

(54) ENDOPROSTHESIS COMPRISING A MAGNESIUM ALLOY

(75) Inventors: Claus Harder, Uttenreuth (DE); Marc Kuttler, Berlin (DE); Bodo Gerold, Zellingen (DE)

(73) Assignee: Biotronik VI Patent AG, Baar (CH)

( * ) Notice: Subject to any disclaimer, the term of this patent is extended or adjusted under 35 U.S.C. 154(b) by 205 days.

This patent is subject to a terminal disclaimer.

(21) Appl. No.: 11/221,322

(22) Filed: Sep. 7, 2005

(65) Prior Publication Data

US 2006/0052863 A1 Mar. 9, 2006

(30) Foreign Application Priority Data

Sep. 7, 2004 (DE) .......................... 10 2004 043 231

(51) Int. Cl.
| | |
|---|---|
| *C22C 23/00* | (2006.01) |
| *A61F 2/915* | (2013.01) |
| *A61L 27/04* | (2006.01) |
| *A61L 27/58* | (2006.01) |
| *A61L 31/14* | (2006.01) |
| *A61F 2/91* | (2013.01) |
| *A61L 31/02* | (2006.01) |

(52) U.S. Cl.
CPC . *A61F 2/91* (2013.01); *A61F 2/915* (2013.01); *A61F 2002/91558* (2013.01); *A61L 27/047* (2013.01); *A61F 2002/91533* (2013.01); *A61L 27/58* (2013.01); *A61L 31/148* (2013.01); *A61L 31/022* (2013.01)
USPC .......................................... 148/420; 420/402

(58) Field of Classification Search
USPC ........................................ 148/420; 420/402
See application file for complete search history.

(56) References Cited

U.S. PATENT DOCUMENTS

| | | | |
|---|---|---|---|
| 2,219,056 | A | 10/1940 | Sauerwald et al. |
| 3,687,135 | A | 8/1972 | Stroganov et al. |
| 4,401,621 | A | 8/1983 | Unsworth et al. |
| 6,206,916 | B1 | 3/2001 | Furst |

(Continued)

FOREIGN PATENT DOCUMENTS

| | | |
|---|---|---|
| DE | 10118603 A1 | 10/2002 |
| DE | 10163106 A1 | 7/2003 |

(Continued)

OTHER PUBLICATIONS

Morgan, J. E.;Mordike, B.L., Development of creep resistant magnesium rare earth alloys, Strength Met. Alloys, Proc. Int. Conf., 6th (1983), Meeting Date 1982, vol. 2, 643-8. Editor: Gifkins, R. C. Publisher: Pergamon, Oxford, UK.*

(Continued)

*Primary Examiner* — Sikyin Ip
(74) *Attorney, Agent, or Firm* — Greer, Burns & Crain, Ltd.

(57) ABSTRACT

An endoprosthesis, in particular an intraluminal endoprosthesis such as a stent, includes a carrier structure, which includes at least one component containing a magnesium alloy of the following composition:
Magnesium: between about 60.0 and about 88.0% by weight
Rare earth metals: between about 2.0 and about 30.0% by weight
Yttrium: between about 2.0% and about 20.0% by weight
Zirconium: between about 0.5% and about 5.0% by weight
Balance: between 0 and about 10.0% by weight
wherein the alloy components add up to 100% by weight.

3 Claims, 2 Drawing Sheets

(56) References Cited

U.S. PATENT DOCUMENTS

| | | |
|---|---|---|
| 6,287,332 B1 | 9/2001 | Bolz et al. |
| 6,544,357 B1 | 4/2003 | Hehmann et al. |
| 6,676,697 B1 | 1/2004 | Richter |
| 6,854,172 B2 * | 2/2005 | Kaese et al. ............. 29/412 |
| 6,979,347 B1 | 12/2005 | Wu et al. |
| 2002/0004060 A1 | 1/2002 | Heublein et al. |
| 2003/0129074 A1 | 7/2003 | Bronfin et al. |
| 2004/0098108 A1 | 5/2004 | Harder et al. |
| 2004/0241036 A1 | 12/2004 | Meyer-Lindenberg et al. |
| 2005/0079088 A1 | 4/2005 | Wirth et al. |
| 2006/0052863 A1 | 3/2006 | Harder et al. |
| 2006/0246107 A1 * | 11/2006 | Harder et al. ............. 424/426 |
| 2007/0191708 A1 | 8/2007 | Gerold et al. |
| 2007/0227629 A1 | 10/2007 | Gerold et al. |
| 2008/0031765 A1 | 2/2008 | Gerold et al. |
| 2008/0033530 A1 | 2/2008 | Zberg et al. |
| 2008/0041500 A1 | 2/2008 | Bronfin et al. |
| 2008/0103594 A1 | 5/2008 | Loffler et al. |
| 2008/0138236 A1 | 6/2008 | Bae et al. |
| 2008/0183278 A1 | 7/2008 | Atanasoska et al. |
| 2008/0193322 A1 | 8/2008 | Gibson et al. |
| 2008/0195198 A1 | 8/2008 | Asgari |

FOREIGN PATENT DOCUMENTS

| | | |
|---|---|---|
| EP | 1 552 856 | 7/1997 |
| EP | 1338293 * | 8/2003 |
| EP | 1419793 * | 5/2004 |
| FR | 1412298 A | 10/1964 |
| FR | 2223471 * | 10/1974 |
| GB | 1067915 A | 5/1967 |
| GB | 1378281 A | 12/1974 |
| JP | 57210946 A | 12/1982 |
| JP | 2001511049 T | 8/2001 |
| JP | 2004-160236 A | 6/2004 |
| WO | WO 02/100452 A1 | 12/2002 |
| WO | 2004/001087 A1 | 12/2003 |
| WO | WO 2004/043474 A2 | 5/2004 |
| WO | 2005/065737 A1 | 7/2005 |

OTHER PUBLICATIONS

Hu, Wangyu; Xu, Huaide; Shu, Xiaolin; Yuan, Xiaojian; Gao, Bingxiang; and Zhang, Bangwei; Calculation of thermodynamic properties of Mg-Re (Re=Sc, Y, Pr, Nd, Gd, Tb, Dy, Ho or Er) alloys by an analytic modified embedded atom method, J. Phys. D:Appl. Phys. 33 (2000) 711-718.*
Housh, S.; Mikucki, B.; and Stevenson, A., Properties of Magnesium Alloys, Properties and Selection: Nonferrous Alloys and Special-Purpose Materials, vol. 2, ASM Handbook, ASM International, WE54, 1990, p. 480-516.*
Housh, S.; Mikucki, B.; and Stevenson, A., Properties of Magnesium Alloys, Properties and Selection: Nonferrous Alloys and Special-Purpose Materials, vol. 2, ASM Handbook, ASM International, WE43, 1990, p. 480-516.*
Heublein et al., "Biocorrosion of magnesium alloys: a new principle in cardiovascular implant technology?," Heart, p. 651-656, (2003).
German Search Report for Application No. 10 2004 026 104, Jan. 12, 2005.
English Translation of Official Letter for Japanese Patent Application No. 2003-383386; Apr. 9, 2009.
Dimario et al., Durg-Eluting Bioabsorbable Magnesium Stent, Journal of Inventional Cardiology, vol. 17, No. 6, 2004 pp. 391-395.
Haferkamp et al.; Alloy Development, Processing and Applications in Magnesium Lithium Alloys, Materials Transactions, 2001, vol. 42, No. 7, pp. 1160-1166.
Housh et al., Properties of Magnesium Alloys in ASM International Metals Handbook, vol. 2, (Properties and Selection-Nonferrous Alloys and Special Purpose Materials), Electronic Version Copyright 1997 (based on fourth printing Oct. 1995).
Journal of the American College of Cardiology, Feb. 2000, vol. 35, No. 2, Suppl. 1, pp. 14A-15A, 1041-1090.
Keikinzoku Gakkai Taikai Koen Gaiyo (Summary of lecture given at a conference of the Japan Institute of Light Metals), 1993, vol. 84, pp. 349-350.
Keikinzoku Gakkai Taikai Koen Gaiyo (Summary of lecture given at a conference of The Japan Institute of Light Metals), 2001, vol. 101, pp. 53-54.
Metallovedenie i Termicheskaya Obrabotka Metallov, 1988, No. 2, pp. 29-31, and accompanying English language translation.
Papriov et al., Biodegradable Magnesium Alloys for Medical Applications, Functional Materials, vol. 15, No. 1, 2008, pp. 139-142.
P.G. Seeger, "Magnesium—ein unenbehrlicher Mineralstoff," 1990; pp. 14-16; Sanum-Post No. 13; and accompanying summary of same in the English language.
Smola, B. et al, Structural Aspectsof High Performance Mg Alloys Deisgn, Material Science & Engineering, A; Structural Materials: Properties, Mictrostructure and Processing (2002), A324 (1-2), 113-117.
William Unsworth, Competitive Advances in Metals and Processes, International SAMPE Metals and Metals Processing Conference Series, 1987, vol. 1, pp. 69-78.
W. Unsworth, Magnesium, 1989, vol. 18, No. 3, pp. 1-8.
Mark P. Staiger, Alexis M. Pietak, Jerawala Huadmai, George Dias, Magnesium and its alloys as orthopedic biomaterials: A review, Biomaterials 27 (2006) 1728-1734, Elsevier Ltd.
Gopinath Mani, Marc D. Feldman, Devang Patel, C. Mauli Agrawal, Coronary stents: A materials perspective, Biomaterials 28 (2007) 1689-1710, Elsevier Ltd.
EP 05 10 7617 Search Report, May 21, 2008.

* cited by examiner

ENDOPROSTHESIS COMPRISING A MAGNESIUM ALLOY

BACKGROUND OF THE INVENTION

The invention concerns an endoprosthesis, in particular an intraluminal endoprosthesis such as a stent, having a carrier structure which entirely or in parts comprises a magnesium alloy.

The purpose of many endoprostheses is to implement a support function in the interior of the body of a patient. Accordingly, endoprostheses are designed to be implantable and have a carrier structure which ensures the support function. Implants of metallic materials are known. The choice of metals as the material for the carrier structure of an implant of that nature is based in particular on the mechanical properties of metals.

Metallic stents are known in large numbers. One of the main areas of use of such stents is permanently dilating and holding open vessel constrictions, in particular constrictions (stenoses) of the coronary vessels. In addition, aneurysm stents are also known, which afford a support function for a damaged vessel wall. Stents of that kind generally have a peripheral wall of sufficient carrying strength to hold the constricted vehicle open to the desired amount. In order to permit an unimpeded flow of blood through the stent it is open at both ends. More complicated configurations also permit an unimpeded flow of blood in side vessels (side branch access). The supporting peripheral wall is generally formed by a lattice-like carrier structure which makes it possible for the stent to be introduced in a compressed condition, when it is of small outside diameter, to the constriction to be treated in the respective vessel and there expanded, for example, by means of a balloon catheter, to such a degree that the vessel is of the desired enlarged inside diameter. Basically therefore, the stent is subject to the requirement that its carrier structure in the expanded condition affords a sufficient carrying strength to hold the vessel open. In order to avoid unnecessary vessel damage, it is also desirable that, after expansion and after removal of the balloon, the stent only slightly elastically springs back (recoil) so that upon expansion of the stent it has to be expanded only little beyond the desired final diameter. Further criteria which are desirable in relation to a stent include, for example, uniform surface coverage and a structure which allows a certain degree of flexibility in relation to the longitudinal axis of the stent.

In some cases, such as for example, in relation to screw means for complicated fractures or other connecting and supporting elements in bone surgery, suture materials or in particular in the case of intraluminal endoprostheses such as stents, a durable holding and support function afforded by the endoprosthesis is not required. Rather, in some of those situations of use, the body tissue can recover in the presence of the holding and support prosthesis in such a way that there is no need for an ongoing supporting action by the prosthesis. That has led to the idea of making such prostheses from bioresorbable material.

Besides the desired mechanical properties of a stent, as far as possible, it should interact with the body tissue at the implantation location in such a way that renewed vessel constrictions do not occur, in particular vessel constrictions caused by the stent itself. Re-stenosis (re-constriction of the vessel) should be avoided as much as possible. It is also desirable if the stent is, as far as possible, responsible for no, or only a very slight, inflammatory effect. In regard to a biodegradable metal stent, it is moreover desirable if the decomposition products of the metal stent as far as possible have no, or only very little, negative physiological effects and even positive physiological effects.

DE 197 31 021 discloses a bioresorbable metal stent, the material of which, as its main constituent, contains magnesium, iron or zinc. The mechanical properties, degradation behavior and biocompatibility mean that, in particular, magnesium alloys are to be preferred.

In DE 102 53 634, DE 101 28 100 or EP 1 395 297 the focus is on the use of such biodegradable magnesium alloys for medical purposes such as plates, screws, suture material or stents. The magnesium alloys have a magnesium content of over 70% by weight or over 90% by weight. With an increasing magnesium content however, the degradation time and therewith, the duration of the mechanical integrity required, rapidly decrease. In the case of stent uses, the degradation periods of such alloys are typically markedly less than 30 days. That is inadequate for many uses in medicine. Thus, in regard to stent uses, it has not hitherto been clearly established how long mechanical integrity is required to afford a sufficient supporting function. The estimates from experts vary from a few days to a year. In the case of complicated fractures, the healing process can easily involve 6 months.

Mechanical stability is also extremely important in particular for endoprosthesis uses. It permits the endoprosthesis to be of a compact design configuration while affording adequate stability. In the case of stents for example, the attempt is made to produce ever smaller leg widths as studies have shown that inter alia, the risk of re-stenosis is markedly reduced with the leg width as the leg inter alia mechanically irritates the surrounding tissue. Suitable material strengths are required to achieve that. Magnesium alloys which have been used hitherto, as set forth in DE 102 53 634, DE 101 28 100 or EP 1 395 297, are relatively soft. That limits the area of use as an endoprosthesis.

Besides the mechanical properties, biocompatibility of the alloy employed is essential for use as a medical implant. Alternative biodegradable materials such as for example, polymers, besides the poor mechanical properties, have to contend in particular with the difficulty of a low level of biocompatibility. Magnesium alloys have already exhibited markedly better properties, but it will be noted in this respect that this involves in particular aluminum-bearing alloys as described for example in DE 101 28 100 or EP 1 395 297. In that case, the aluminum is required inter alia for the formation of cover layers which are intended to slow down diffusion of the magnesium and thus the degradation process. According to those publications, that is required inter alia, in order to achieve sufficiently long mechanical stability for the endoprosthesis and to prevent outgassing phenomena in the degradation process.

Aluminum however, is known for causing damage to health, particularly when it is in ionic form. Thus, aluminum is known inter alia for causing damage to the central nervous system and triggering symptoms such as dementia, memory loss, loss of motivation or intense shaking. Aluminum is considered as a risk factor for Alzheimer's disease (Harold D Foster Ph D, Journal für Orthomolekulare Medizin 2/01). Adverse effects in regard to biocompatibility in the immediate proximity of endoprostheses comprising aluminum-bearing magnesium alloys could be detected in experiments. Thus, in animal experiments, pathological halos were observed around degrading legs of such stents as well as pronounced neointima hyperplasia, which counteracts the real purpose of the stent of preventing vessel closure. The use of aluminum in degradable medical implants such as in particular stents is thus not to be favored.

Hitherto, the approach in relation to medical implants involving activating the healing processes of the body itself, in the context of using endoprostheses, in order in that way further to improve the healing process, has been generally neglected.

SUMMARY OF THE INVENTION

With that background in mind, an aspect of the present invention is to provide a biodegradable endoprosthesis based on a magnesium alloy, which avoids the outlined disadvantages of the state of the art. In particular the invention aims to provide alloys enjoying enhanced mechanical stability and longer degradation times.

In accordance with the invention, that aspect is attained by an endoprosthesis that has a carrier structure which entirely or in parts comprises a magnesium alloy of the following composition:

Magnesium: between about 60.0 and about 88.0% by weight
Rare earth metals: between about 2.0 and about 30.0% by weight
Yttrium: between about 2.0% and about 20.0% by weight
Zirconium: between about 0.5 and about 5.0% by weight, and
Balance: between 0 and about 10.0% by weight wherein the alloy components add up to 100%. The alloy exhibits very advantageous mechanical but also physiological properties and a degradation behavior in vivo which is delayed in relation to the known alloys. It can be easily processed and in initial studies exhibits a positive physiological effect on the surrounding tissue in a human and an animal if the alloy is used in endoprostheses, in particular stents.

The collective term 'rare earth metal' stands for the elements scandium (atomic number 21), lanthanum (57) and the 14 elements following lanthanum: cerium (58), praseodymium (59), neodymium (60), promethium (61), samarium (62), europium (63), gadolinium (64), terbium (65), dysprosium (66), holmium (67), erbium (68), thulium (69), ytterbium (70) and lutetium (71), which are referred to as lanthanides. The proportion of the rare earth metals in the magnesium alloy thus also includes the proportion of neodymium. The latter proportion—if present—is also related to the total weight of the alloy and must be in the specified range. If the proportion of neodymium in the alloy is for example 2.0% by weight and the proportion of rare earth metals is about 2.5% by weight, then necessarily rare earth metals, besides neodymium, have a proportion by weight in the alloy of about 0.5% by weight.

An alloy with a magnesium proportion of between about 60.0 and about 70.0% by weight is particularly preferred. The alloy has a degradation behavior which is delayed in relation to the state of the art but it is still sufficiently biodegradable. The alloy and the decomposition products exhibited good biological compatibility, that is to say, in initial tests no immunological reactions or inflammations occurred.

The balance preferably contains only the impurities caused by the magnesium alloy production process. In other words, the composition preferably only contains specific impurities which cannot be avoided in production of the alloy or residual components which are deliberately added to the alloy. That ensures and in part even first attains the positive physiological effects and the mechanical properties of the material.

Supplemental to or alternatively to the above-indicated preferred variant the balance contains no or at most <0.01% by weight of aluminum. It is precisely aluminum that has a pronounced adverse influence on physiological behavior as material investigations both in vivo and in vitro have shown.

By virtue of the adverse properties, in particular on biocompatibility, besides the element aluminum (Al), preferably also the elements copper (Cu), nickel (Ni), silver (Ag), mercury (Hg), cadmium (Cd), beryllium (Be) or chromium (Cr) are also avoided in the alloys; that is to say, the elements are not contained in the alloy, apart from impurities caused by the manufacturing procedure. The proportion in the alloy referred to as the balance contains as a matter of priority proportions by mass of one, more or all of the stated elements, under the following limits:

Aluminum<0.01% by weight,
Copper<0.03% by weight,
Nickel<0.005% by weight.
Silver<0.01% by weight,
Mercury<0.03% by weight,
Cadmium<0.03% by weight,
Beryllium<0.03% by weight,
Chromium<0.03% by weight.

Avoiding those elements is of significance in terms of the purpose of the invention as they have an effect which is damaging to health, they undesirably influence the mechanical properties of the alloy and they adversely affect the influences of the alloy and in particular, magnesium, which are positive influences in terms of the healing process. As is known, just slight traces of impurities can have a metallurgically and/or physiologically considerable effect. Identifying the troublesome elements and in particular, establishing limit values in respect of those elements therefore affords a considerable technical contribution to optimizing the products.

It is preferred, in contrast, for the balance to contain one or more elements from the group consisting of lithium, zinc, iron, titanium, tantalum, molybdenum and tungsten. The proportion of the components in the alloy is preferably between 0.1 and 0.5% by weight, wherein the cumulated overall proportion thereof is at a maximum 10.0% by weight. The presence of those elements evidently positively influences the degradation behavior, the mechanical properties and biocompatibility of the implant.

Tantalum, molybdenum and tungsten are made responsible inter alia for improved mechanical stability. In addition, the X-ray visibility of the alloy is improved. Also, titanium which is known to be extremely biocompatible has a marked influence on mechanical stability.

Like magnesium, zinc and iron can be identified as biodegradable by virtue of their corrosion behavior and fundamental significance in terms of metabolic processes in the body. Inter alia, corrosion behavior and corrosion rate can be influenced by way of those elements.

It is further preferred for the proportion of neodymium to be between 0.5 and 10.0% by weight, in particular between 2.0 and 2.5% by weight, of the alloy. That makes it possible to still further increase the physiological compatibility of the alloy and its decomposition products and to optimise the degradation behavior for the intended purposes.

The magnesium alloy described herein made it possible to achieve a significantly improved degradation process with markedly better reproducibility than is known hitherto for example for aluminum-bearing magnesium alloys (Heart (2003) 89, 691-656). In particular, reproducibility of the degradation process is indispensable for a medical use. By virtue of the controlled and slow degradation process embodied, no, or at worst slight, outgassing phenomena occur.

It was demonstrated in vivo and in vitro that the alloy and the decomposition products thereof are extremely biocompatible. By using the magnesium alloy, it was possible to counteract severe immunological reactions on the part of the body. Controlled cell growth, in particular in respect of human smooth muscle cells and endothelium cells, could be demonstrated on the basis of in vitro tests. Uncontrolled cell proliferation phenomena which can lead to re-stenosis appear to be prevented or greatly checked. That is not the case in that respect, in particular when using aluminum-bearing alloys in respect of which severe neointima hyperplasia was observed. The operative mechanism on which the positive effects are based has not hitherto been discovered in detail.

Magnesium could afford a contribution to the particular compatibility of the implant. Generally known effects and influences of magnesium, which is usually absorbed by way of food, on the body functions lead to the assumption that such processes are also at least locally activated when using magnesium as an implant in a suitable alloy composition.

It is known for example that magnesium in an organism has a positive influence on wound healing, as it is necessary for anaerobic metabolism and promotes normal granulation of the connective tissue and rather prevents uncontrolled cell growth (Dr med Dr sc Nat PG Seeger, SANUM-Post No 13/1990, 14-16).

A further positive aspect when using magnesium is that the non-specific defense by way of the properdin system is operative only when magnesium is present and phagocytosis of bacteria by leucocytes experiences a stimulus by magnesium. Accordingly, magnesium provides, inter alia, for combating infections by promoting or activating the immune system of the body and reduces susceptibility to infections. Unwanted inflammation phenomena caused by infection, because of contamination which can occur in the context of using an endoprosthesis, and which in turn can be triggers for re-stenosis, are thus counteracted.

The alloy used here also has a positive action against mechanically induced re-stenosis. That is achieved on the one hand, by the mechanical properties of the alloy used, which are distinguished by a favorable modulus of elasticity. In addition, the generally known muscle-relaxing action of magnesium (Ca antagonist) is used to reduce mechanical irritations. It is to be expected that the magnesium in the alloy or the magnesium-bearing decomposition products upon degradation promote relaxation of the muscle cells in the more immediate proximity. That is advantageous, in particular in relation to stent uses, as not only is mechanical irritation reduced but also the vessel can be additionally held open by the locally relaxed muscle tissue.

The magnesium alloy is preferably extruded. It has been found that processing of the alloy influences the physiological effect thereof. Those physiological properties are thus at least in part governed by the production process.

The endoprosthesis is preferably in the form of an intraluminal endoprosthesis. A particularly preferred endoprosthesis is one which is in the form of a stent, more particularly a coronary stent or a peripheral stent. By virtue of the positive properties of the specified magnesium alloy, the carrier structure of the endoprosthesis preferably entirely consists of the magnesium alloy.

In accordance with a preferred variant for use of the alloy as a stent, in particular as a coronary stent or as a peripheral stent, the specific composition of the magnesium alloy as well as the modification thereof is predetermined by the mode of manufacture and the stent design to the effect that decomposition starts immediately after implantation and mechanical integrity is maintained for between at least 5 days and at most 1 year. In that respect, the term 'mechanical integrity' is used to denote the stability, which is still sufficient in spite of progressing decomposition, of the structural elements of the implant, which serve to fulfil the medical purpose of the implant; that is to say, maintaining the required supporting function. In a particularly preferred feature, the period of time is between 10 and 90 days.

BRIEF DESCRIPTION OF THE SEVERAL VIEWS OF THE DRAWINGS

The invention will now be described in greater detail by means of an embodiment with reference to the Figures in which.

DETAILED DESCRIPTION OF THE INVENTION

Figure 1:
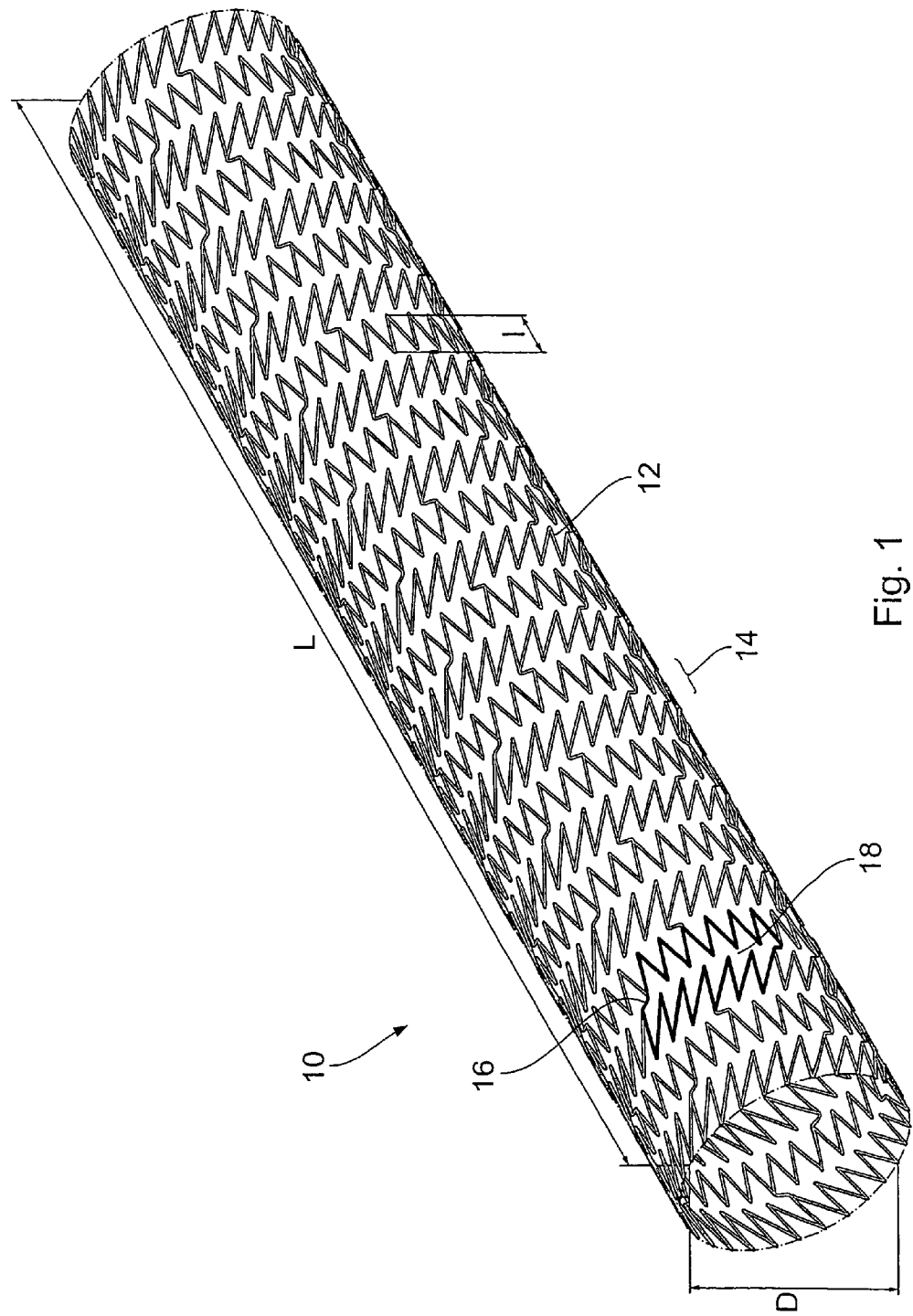
FIG. 1 shows a diagrammatic view of an endoprosthesis in the form of a stent.

FIG. 1 shows an endoprosthesis as an endoluminal prosthesis in the form of a stent 10 having a carrier structure. The stent 10 and its carrier structure are in the form of a hollow body which is open at its ends and the peripheral wall of which is formed by the carrier structure which in turn is formed by partially folded legs 12. The legs 12 form support portions 14 which are each formed by a leg 12 which is closed in an annular configuration in the longitudinal direction and which is folded in a zig-zag or meander-shaped configuration. The stent 10 is suitable for coronary use.

The carrier structure of the stent 10 is formed by a plurality of such support portions 12 which occur in succession in the longitudinal direction. The support portions or leg rings 14 are connected together by way of connecting legs 16. Each two connecting legs 16 which are mutually adjacent in the peripheral direction and the parts, which are in mutually opposite relationship between those connecting legs 16, of the leg rings 14 or support portions 12 define a mesh 18 of the stent 10. Such a mesh 18 is shown emphasized in FIG. 1. Each mesh 18 encloses a radial opening in the peripheral wall or the carrier structure of the stent 10.

Each leg ring 14 has between some three and six connecting legs 16 which are distributed equally over the periphery of the stent 10 and which respectively connect a leg ring 14 to the adjacent leg ring 14. Accordingly, the stent 10 has between three and six respective meshes 18 in the peripheral direction between two support portions 14.

The stent 10 is expandable in the peripheral direction by virtue of the folding of the legs 12. That is effected for example, by means of a per se known balloon catheter which, at its distal end, has a balloon which is expandable by means of a fluid. The stent 10 is crimped onto the deflated balloon, in the compressed condition. Upon expansion of the balloon, both the balloon and also the stent 10 are enlarged. The balloon can then be deflated again and the stent 10 is released from the balloon. In that way, the catheter can serve simultaneously for introducing the stent 10 into a blood vessel and in particular, into a constricted coronary vessel and also for expanding the stent 10 at that location.

Figure 2:
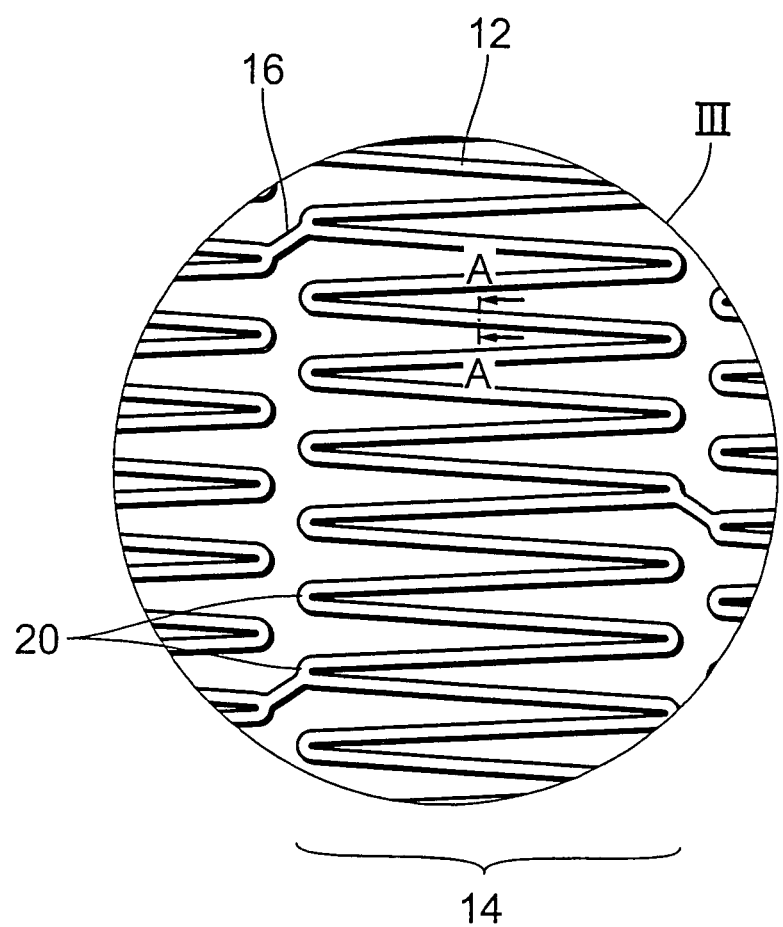
FIG. 2 shows a development of the carrier structure of the stent shown in FIG. 1.

FIG. 2 shows a portion from a development of the peripheral wall of the stent 10. The development shows the compressed condition of the stent 10.

The carrier structure of the stent 10 shown in the Figures completely consists of a biodegradable magnesium alloy of the following composition:

Magnesium: 65% by weight
Rare earth metals: 15.0% by weight, with neodymium 2.3% by weight
Yttrium: 10.0% by weight Zirconium: 3.0% by weight
Lithium: 3.0% by weight
Iron: 2.0% by weight
Zinc: 2.0% by weight
Aluminum, silver, copper, mercury, cadmium, beryllium, chromium and nickel: <0.005% by weight * (* detection limit in determination), wherein the alloy components add up to 100% by weight.

The invention claimed is:

1. An endoprosthesis comprising a carrier structure which includes at least one component comprising a magnesium alloy of the following composition:
   Magnesium: about 65.0% by weight
   Rare earth metals: about 15.0% by weight, with Neodymium about 2.3% by weight out of the 15.0%
   Yttrium: about 10.0% by weight
   Zirconium: about 3.0% by weight
   Lithium: about 3.0% by weight
   Iron: about 2.0% by weight
   Zinc: about 2.0% by weight
   wherein a balance comprising of alloy components adds up to 100% by weight of the alloy; and
   wherein the balance comprises any element other than magnesium, rare earth metals, neodymium, yttrium, zirconium, lithium, iron and zinc.

2. The endoprosthesis of claim 1, wherein the balance may further comprise any element of the group consisting of titanium, tantalum, molybdenum and tungsten.

3. The endoprosthesis of claim 1, wherein the endoprosthesis is in the form of one of an intraluminal endoprosthesis, a coronary stent and a peripheral stent.

* * * * *